US006666838B2

(12) United States Patent
Modglin et al.

(10) Patent No.: US 6,666,838 B2
(45) Date of Patent: Dec. 23, 2003

(54) LOW-PROFILE LUMBO-SACRAL ORTHOSIS

(75) Inventors: Michael D. Modglin, Braselton, GA (US); Debusk O. V. Autry, Knoxville, TX (US)

(73) Assignee: DeRoyal Industries, Inc., Powell, TN (US)

( * ) Notice: Subject to any disclaimer, the term of this patent is extended or adjusted under 35 U.S.C. 154(b) by 47 days.

(21) Appl. No.: 10/127,326

(22) Filed: Apr. 22, 2002

(65) Prior Publication Data

US 2003/0199799 A1 Oct. 23, 2003

(51) Int. Cl.[7] .................................................. A61F 5/00
(52) U.S. Cl. ........................ 602/19; 128/876; 128/100.1
(58) Field of Search ................................. 128/869, 876, 128/873–875, 96.1, 100.1; 602/19, 5; 2/255, 237, 238

(56) References Cited

U.S. PATENT DOCUMENTS

| | | |
|---|---|---|
| 2,100,964 A | 11/1937 | Kendrick |
| 3,926,183 A | 12/1975 | Spiro |
| 3,927,665 A | 12/1975 | Wax |
| 4,099,524 A | 7/1978 | Cueman et al. |
| 4,120,297 A | 10/1978 | Rabischong et al. |
| 4,175,553 A | 11/1979 | Rosenberg |
| 4,459,979 A | 7/1984 | Lewis, Jr. |
| 4,470,417 A * | 9/1984 | Gruber ................ 128/DIG. 15 |
| 4,475,543 A | 10/1984 | Brooks et al. |
| 4,489,676 A | 12/1984 | Colquist |
| 4,508,110 A | 4/1985 | Modglin |
| 4,559,933 A | 12/1985 | Batard et al. |
| 4,821,739 A | 4/1989 | Willner et al. |
| 5,074,288 A | 12/1991 | Miller |
| 5,188,585 A | 2/1993 | Peters |
| 5,241,704 A | 9/1993 | Sydor |
| 5,259,831 A | 11/1993 | LeBorn |
| 5,267,948 A | 12/1993 | Elliott |
| 5,302,171 A | 4/1994 | Pearson et al. |

(List continued on next page.)

OTHER PUBLICATIONS

Declaration of Michael D. Modglin.
Pictures Fetherlite brace made by National Orthotic Laboratories, Inc., bearing Patent No. 4,508,110, sold 1994.
National Orthotic Laboratories, Inc., catalog, 1994.
Pictures Mirage prototype brace made by Michael D. Modglin, 1995.
Pictures Kittle prototype; brace made by Michael D. Modglin, 1995.
Letter Mike Modglin to Mr. Jerry Kittle, Nov. 8, 1995.

*Primary Examiner*—Michael A. Brown
(74) *Attorney, Agent, or Firm*—Smith, Gambrell & Russell, LLP

(57) ABSTRACT

A low-profile lumbo-sacral orthosis consists of flexible anterior and posterior members, both shaped to fit around the waist of a patient's torso, and a closure system on each side of the orthosis for joining the flexible anterior and posterior members. The anterior member is formed of a web of flexible material. A middle panel of loop material is attached to external surface of the anterior web in the middle to form a pocket, and two anterior side panels of loop material are attached to external surface of the anterior web at each side to form pockets. Reinforcing splints are inserted into each pocket. The flexible posterior member is formed of a web of flexible material with two posterior side panels of loop material attached to the external surface to form two pockets. Reinforcing splints are inserted into each of the pockets. A moldable posterior splint is attached to the external surface of the posterior web in the middle. Each closure system consists of a plurality of straps and buckles connected to attachment strip. The straps are connected to the anterior attachment strip, extend through the plurality of buckles on the posterior attachment strip, and terminating in a common strap.

13 Claims, 3 Drawing Sheets

U.S. PATENT DOCUMENTS

| | | |
|---|---|---|
| 5,362,304 A | 11/1994 | Varn |
| 5,399,151 A | 3/1995 | Smith |
| 5,437,614 A | 8/1995 | Grim |
| 5,499,965 A | 3/1996 | Sanchez |
| 5,537,690 A | 7/1996 | Johnson |
| 5,560,046 A | 10/1996 | Iwamasa et al. |
| 5,632,723 A | 5/1997 | Grim |
| 5,634,891 A | 6/1997 | Beczal, Sr. et al. |
| 5,656,020 A | 8/1997 | Greengarg |
| 5,693,006 A | 12/1997 | Slautterback |
| 5,718,670 A * | 2/1998 | Bremer ........................ 602/19 |
| 5,722,940 A | 3/1998 | Gaylord, Jr. et al. |
| 8,853,378 | 12/1998 | Modglin |
| 5,967,998 A * | 10/1999 | Modglin .................. 128/100.1 |
| 6,478,759 B1 * | 11/2002 | Modglin et al. .............. 602/19 |

\* cited by examiner

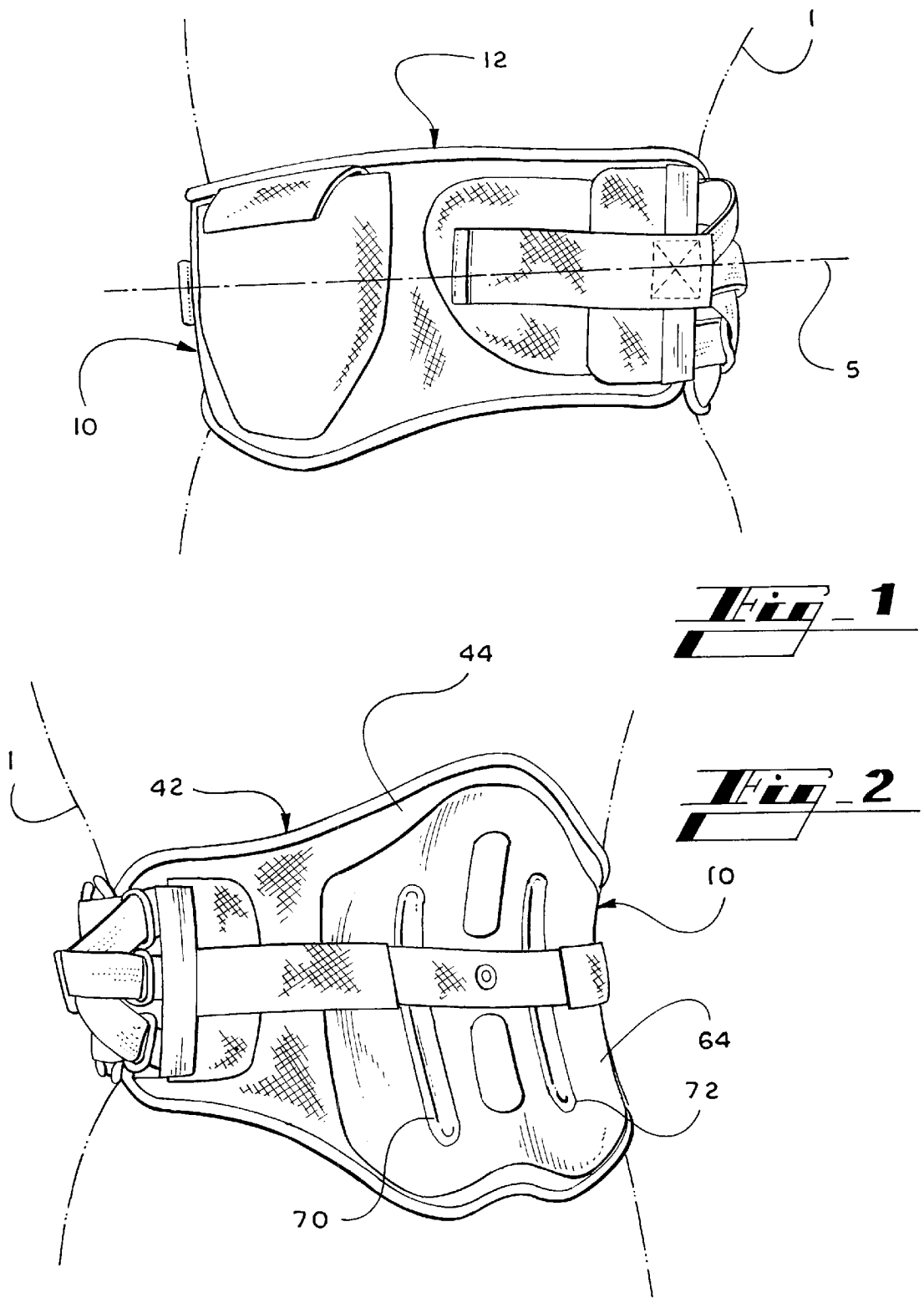

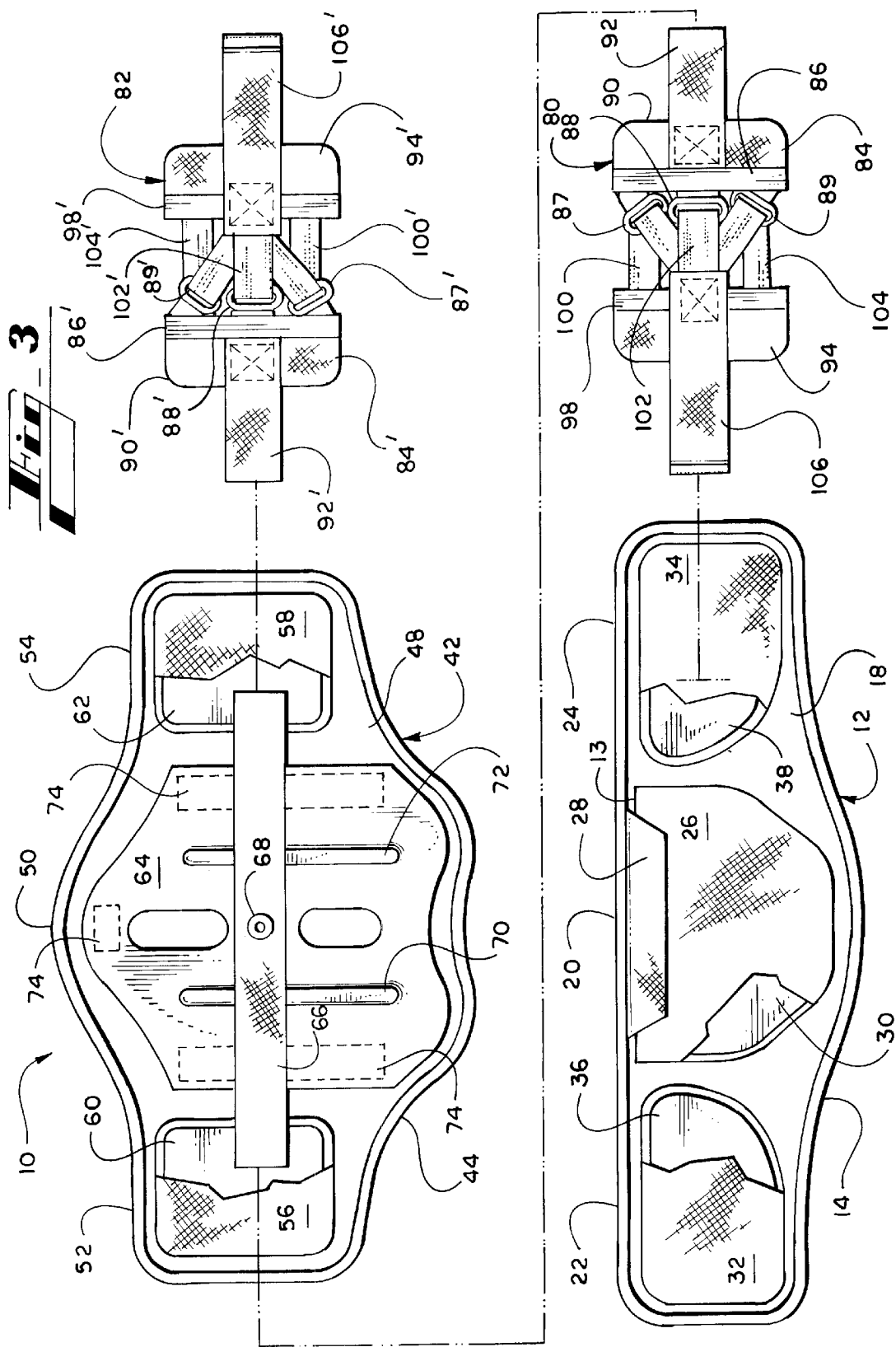

LOW-PROFILE LUMBO-SACRAL ORTHOSIS

FIELD OF THE INVENTION

The present invention relates to a lumbo-sacral orthosis and relates particularly to a low profile, soft flexible lumbo-sacral orthosis or back brace.

BACKGROUND OF THE INVENTION

Soft flexible orthopedic back braces and rigid body jackets support a patient's spine in connection with postoperative fusion and trauma injuries. One such soft flexible orthopedic back brace is disclosed in U.S. Pat. No. 5,967,998, which is assigned to the assignee of the present invention. In addition, one such rigid body jacket is disclosed in U.S. Pat. No. 4,508,110. Such soft flexible back braces and rigid body jackets are sized to extend along the majority of the length of the patient's spine in order to immobilize the patient's spine.

Where a patient experiences mild low back pain, lumbar muscle weakness, lumbar strain or sprain, or mechanical or discogenic lumbar pain, the soft flexible back brace and the rigid body jacket disclosed in the above identified patents may not offer appropriate treatment. While the soft flexible back brace and the rigid body jacket disclosed in the above identified patents provide sufficient support and relief for conditions localized in the lumbar region of the spine, these longer soft flexible back brace and rigid body jacket are not required and may be cumbersome and uncomfortable for a patient who has a less severe condition than the conditions for which the prior art soft flexible back brace and rigid body jacket are prescribed.

For the conditions of mild low back pain, lumbar muscle weakness, lumbar strain or sprain, or mechanical or discogenic lumbar pain, a low profile lumbo-sacral orthosis is generally indicated. Moreover, because the lumbar conditions identified above may be mild, the lumbo-sacral orthosis used to treat such conditions must be comfortable, easy to don and doff, adjustable to a variety of patient figures, and simple and low cost to manufacture.

SUMMARY OF THE INVENTION

A low profile lumbo-sacral orthosis, which is useful in the treatment of mild low back pain, lumbar muscle weakness, lumbar strains or sprains, or mechanical or discogenic lumbar pain, comprises a low profile, soft flexible back brace. Such a low-profile lumbo-sacral orthosis may be used for proprioceptive feedback, posture control, and the reinforcement of proper body ergonomics.

The low-profile lumbo-sacral orthosis of the present invention consists of a flexible anterior member shaped to fit adjacent the waist of a patient's torso, a flexible posterior member shaped to fit adjacent the waist of a patient's torso, and a closure system on each side of the low-profile lumbo-sacral orthosis for joining the flexible anterior member to the flexible posterior member.

The anterior member of the lumbo-sacral orthosis is constructed of a web of flexible, breathable material. The anterior web is divided into an anterior middle section and two anterior side sections. A middle panel of loop material is attached to the external surface of the anterior web at the anterior middle section to form an anterior middle pocket. Anterior side panels of loop material are attached to the external surface of the anterior web at each anterior side section to form anterior side pockets. An anterior splint is inserted into the anterior middle pocket, and anterior reinforcing inserts are inserted into each of the anterior side pockets of the anterior member.

The posterior member is constructed of a posterior web of flexible, breathable material. The posterior web is divided into a posterior middle section and two posterior side sections. Posterior side panels of loop material are attached to the external surface of the posterior web at each posterior side section to form posterior side pockets. Posterior reinforcing inserts are enclosed within each of the posterior side pockets of the posterior member. A posterior splint is attached to the external surface of the posterior web at the posterior middle section. The posterior splint has a splint strap of loop material secured to the center of the posterior splint. The splint strap extends from the center attachment on the posterior splint in each direction parallel to the waistline of the patient.

A closure system connects the anterior and posterior members together on each side in an adjustable fashion. The adjustable closure system on each side of the lumbo-sacral orthosis enables the lumbo-sacral orthosis to fit a range of body figures and provides adjustable compression around the patient's waist. Each closure system includes a posterior strip of hook and loop material that engages one of the posterior side panels, an anterior strip of hook and loop material that engages one of the anterior side panels, and a set of straps that interconnect the posterior strip and the anterior strip. With respect to the posterior strip of the closure system, a plurality of buckles or chafes are attached to the anterior edge of the posterior strip, and an auxiliary strap of hook and loop material is attached to the posterior edge of the posterior strip of the closure system. With respect to the anterior strip of a closure system, a plurality of straps are attached to the posterior edge of the anterior strip. The straps extend rearwardly from the anterior strip, pass through the plurality of buckles on the posterior strip, and terminate in a common strap of hook and loop material. The common strap connects to the loop material of the anterior side panels or the anterior middle panel depending on the size of the patient and a degree of tension exerted on the common strap. The auxiliary strap engages the splint strap to complete the encirclement of the patient's waist and thereby hold the posterior splint firmly in place.

In fitting the lumbo-sacral orthosis of the present invention, the side closure systems are released to a fully extended condition. One of the side closure systems is then opened by typically releasing the anterior strip from the mating anterior side panel. Once opened, the lumbo-sacral orthosis is wrapped around the waist of the patient and the anterior strip is reconnected to the anterior side panel so that the lumbo-sacral orthosis is loosely fit around the patient's waist. The patient then lies in the supine position. While in the supine position, the patient grasps the single common straps on each side of the orthosis and pulls the common straps forward to tighten the orthosis. Once the orthosis is sufficiently tightened, the common straps with their hook material are pressed against the loop material on the anterior panels of the anterior member to secure the orthosis in the tightened state. The degree of pressure exerted in pulling the common straps forward determines the degree of pressure exerted by the orthosis around the waist of the patient.

In order to insure correct support by the lumbo-sacral orthosis, the posterior splint may require reshaping. Such reshaping may be required in order to match the contour of the patient's spine and the need for support at certain positions along the patient's spine. The posterior splint is made from a heat moldable plastic that can be heated in localized areas by means of a heat gun in order to change the shape of the contour of the posterior splint. In addition, the posterior splint has reinforcing ridges, running a perpendicular to the waistline of the patient. The reinforcing ridges, however, should not be heated and softened during the fitting of the brace to the patient in order to maintain the structural integrity of the posterior splint.

BRIEF DESCRIPTION OF THE DRAWINGS

FIG. 1 is an anterior perspective view of the lumbo-sacral orthosis of the present invention.

FIG. 2 is a posterior perspective view of the lumbo-sacral orthosis of the present invention.

FIG. 3 is an exploded view of the components of the lumbo-sacral orthosis of the present invention.

DETAILED DESCRIPTION OF THE PREFERRED EMBODIMENT

Figure 4:
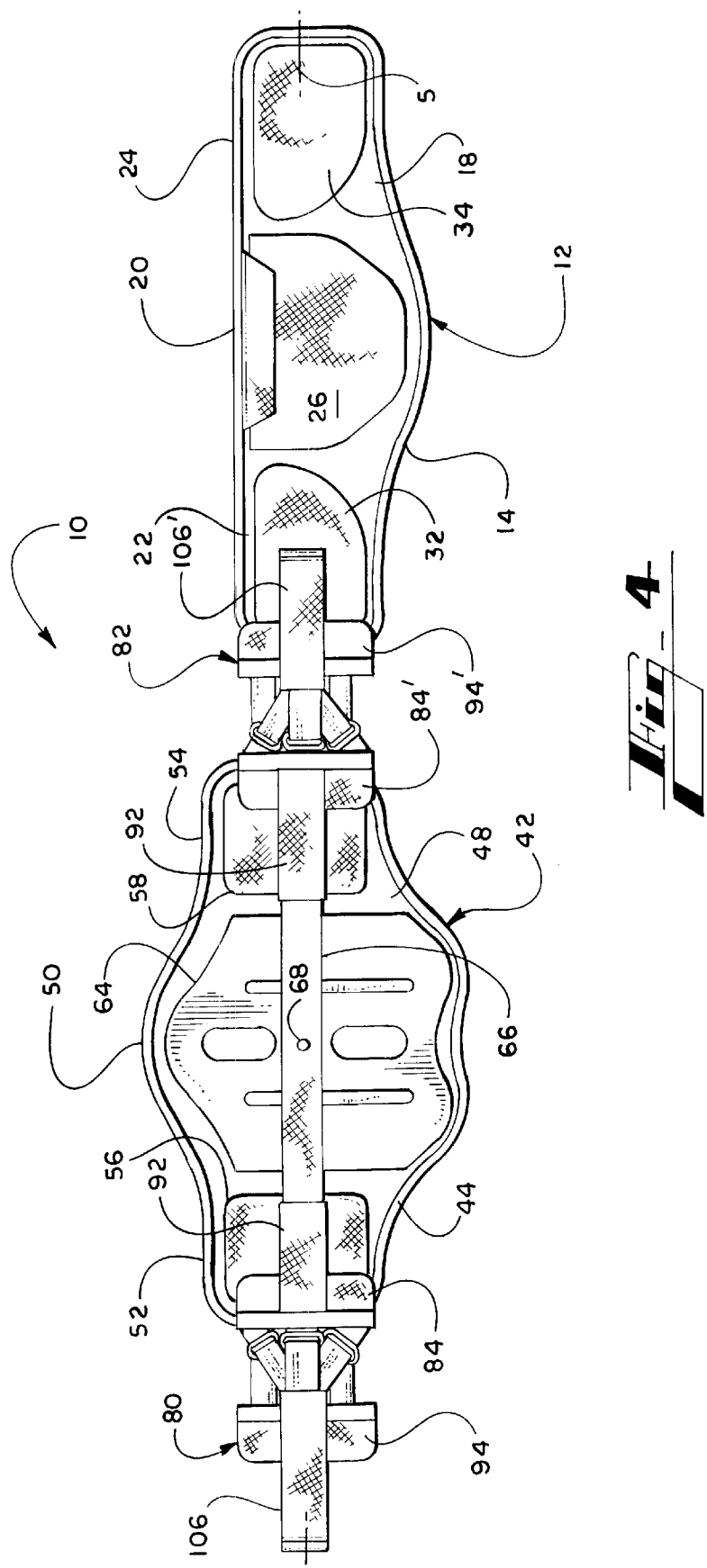
FIG. 4 is an elevation view of the lumbo-sacral orthosis of the present invention.

Referring to the drawings of FIGS. 1–4, a lumbo-sacral orthosis 10 is used for the treatment of mild low back pain, lumbar muscle weakness, lumbar strain or sprain, or mechanical or discogenic lumbar pain. The lumbo-sacral orthosis 10 may be used in connection with lower lumbar strains and sprains, proprioceptive feedback, posture control, and the reinforcement of proper body ergonomics.

The lumbo-sacral orthosis 10 is a low-profile, soft flexible back brace. Particularly, the lumbo-sacral orthosis 10 comprises a flexible anterior member 12 shaped to fit adjacent the waist 5 of a patient's torso 1, a flexible posterior member 42 shaped to fit adjacent the waist 5 of the patient's torso 1, a left closure system 80, and a right closure system 82 which together adjustably join the flexible anterior member 12 to the flexible posterior member 42.

The flexible anterior member 12 is constructed of an anterior web 14 which has a middle section 20, a right side section 22, and a left side section 24. "Left" and "right" refer to the left and right side of the torso of the patient when the orthosis 10 is being worn by the patient. The web 14 is constructed from a soft breathable material with an external surface 18 which is compatible with conventional hook and loop fastening materials. One such material for the web 14 is a knit/foam/knit laminate. One such knit/foam/knit laminate is available under the mark ORTHO-WICK from Velcro USA Inc., 406 Brown Avenue, Manchester, N.H. 03103. Particularly, the external knit surface 18 has sufficient loop elements so that it is readily engaged by the hook element of a conventional hook and loop fastening material.

An anterior middle panel 26 is attached around its periphery to the external surface 18 at the middle section 20 of the anterior web 14 to form an open pocket. The anterior middle panel 26 is sewn to the anterior web 14. Particularly, the anterior middle panel 26 is sewn around its peripheral edges, except the top edge 13 of the middle panel 26 is left unsewn in order to create an opening for the pocket formed by the middle panel 26 and the anterior web 14. Depending on materials used for the anterior middle panel 26 and the anterior web 14, the anterior middle panel 26 may be attached to the anterior web 14 by gluing, by sonic welding, by nonmetallic rivets, or by other means known to those of ordinary skill in the art. The anterior middle panel 26 is constructed from a soft breathable material with loops on its external surface, which loops constitute the loop element of a conventional hook and loop material. The material for middle panel 26 is a knit/loop laminate material and is available under the mark VELCRO from Velcro USA Inc.

A flap 28 is attached to the anterior web 14 adjacent the top edge 13 of the middle panel 26 in order to close the pocket formed by the anterior middle panel 26 and the anterior web 14. The flap 28 is constructed from a tape material having hooks on its internal surface. The hooks on the internal surface of the flap 28 engage the loops on the external surface of middle panel 26 to close the opening of the pocket at edge 13.

An anterior splint 30 may be inserted in the pocket formed by middle panel 26 in order to maintain the shape of the flexible anterior member 12 at the anterior middle section and to provide compressive support to the abdomen of the patient. The anterior splint 30 is constructed from a rigid, moldable plastic material that can be heated and molded to conform to the patient to provide proper fit and support. Such plastic material for splint 30 includes polypropylene, low density polyethylene, and acrylonitrile butadiene styrene (ABS). One such ABS material is 0.090 inch in thickness and is available from Spartech Corporation, 120 South Central Avenue, Suite 1700, Clayton, Mo. 63105.

Anterior side panels, including a right anterior panel 32 and a left anterior panel 34, are attached to the external surface 18 at the right section 22 and the left section 24 respectively of the anterior web 14 to form side pockets. The anterior side panels 32 and 34 are sewn around their peripheral edges to the anterior web 14. Depending on the materials used for the anterior side panels 32 and 34 and the anterior web 14, the anterior side panels 32 and 34 may be attached to the anterior web 14 by gluing, by sonic welding, by nonmetallic rivets, or by other means known to those of ordinary skill in the art. The anterior side panels 32 and 34 are constructed from the same knit/loop laminate material as the anterior middle panel 26.

Prior to completing the attachment of the anterior side panels 32 and 34 to the anterior web 14, anterior side reinforcing inserts, such as a right anterior reinforcing insert 36 and a left anterior reinforcing insert 38, are sandwiched between the anterior web 14 and the right anterior panel 32 and the left anterior panel 34, respectively. The anterior side reinforcing inserts 36 and 38 function to maintain the shape of the flexible anterior web 14 at the right section 22 and the left section 24 of the anterior member 12 and to provide compressive support to the sides of the abdomen of the patient. The anterior side reinforcing inserts 36 and 38 are constructed from a rigid, moldable plastic material that can be heated and molded to conform to the patient and thereby insure proper fit and support. Such plastic material for the anterior side reinforcing inserts 36 and 38 includes low density polyethylene. One such low density polyethylene material is $1/16$ of an inch in thickness and is available from Spartech Corporation.

With continuing reference to FIGS. 3 and 4, the orthosis 10 includes the flexible posterior member 42. The flexible posterior member 42 is constructed of a posterior web 44 which has a middle section 50, a right side section 54, and a left side section 52. Again, "left" and "right" refer to the left and right side of the torso of the patient when the orthosis 10 is being worn by the patient. The posterior web 44 is constructed from the same knit/foam/knit laminate material as the anterior web 14, and the posterior web 44 therefore has a knit external surface 48 which is compatible with a conventional hook and loop material fastener.

Posterior side panels, including a right posterior panel 58 and a left posterior panel 56, are attached to the external surface 48 at the right section 54 and the left section 52 respectively of the posterior web 44 to form side pockets. The posterior side panels 58 and 56 are sewn around their peripheral edges to the posterior web 44. Depending on the materials used for the posterior side panels 58 and 56 and the posterior web 44, the posterior side panels 58 and 56 may be attached to the posterior web 44 by gluing, by sonic welding, by nonmetallic rivets, or by other means known to those of ordinary skill in the art. The posterior side panels 58 and 56 are constructed from the same knit/loop laminate material as the anterior middle panel 26 described above.

Prior to completing the attachment of the posterior side panels 58 and 56 to the posterior web 44, posterior side reinforcing inserts, such as a right posterior reinforcing insert 62 and a left posterior reinforcing insert 60, are sandwiched between the posterior web 44 and the right posterior panel 58 and the left posterior panel 56, respectively. The posterior side reinforcing inserts 62 and 60 function to maintain the shape of the posterior web 44 at the right section 54 and the left section 52 of the posterior member 42 and to provide compressive support to the sides of the back of the patient. The posterior side reinforcing inserts 62 and 60 are constructed from a rigid, moldable plastic material that can be heated and molded to conform to the patient and thereby insure proper fit and support. The plastic material for the posterior side reinforcing inserts 62 and 60 is the same as the plastic material used for the anterior side reinforcing inserts 36 and 38.

In addition to the posterior side reinforcing inserts 62 and 60, the flexible posterior member 42 also includes a posterior splint 64. As best seen in FIG. 2, the posterior splint 64 has a convex profile to fit the lower back of the patient 1. The convex shape of the posterior splint 64 is maintained by reinforcing ridges 70 and 72 extending perpendicular to the waistline 5 of the patient 1. A splint strap 66 is attached to the posterior splint 64 by means of a plastic rivet 68. The posterior splint 64 is centered on the posterior web 44 as shown in FIG. 3. While not being worn by the patient 1, the posterior splint 64 is conveniently anchored to the posterior web 44 by means of attachment tabs, such as tab 74, at each of the four corners of the splint 64 (FIG. 3). The attachment tabs are hook material with the non hook or plain side glued to the posterior splint 64 so that the hook side can engage the knit exterior surface 48 of the posterior web 44. Consequently, the posterior splint 64 remains properly positioned on the posterior web 44 during donning and doffing of the orthosis 10. The posterior splint 64 is constructed from a heat moldable plastic material such as 0.090 inch thick ABS from Spartech Corporation. Particularly, the material for the posterior splint 64 is heat moldable, lightweight, rigid, and inexpensive.

The flexible anterior member 12 and the flexible posterior member 42 are joined together at each side of the patient by means of the left closure system 80 and the right closure system 82. The closure systems 80 and 82 are mirror images of each other. The following description of the left closure system 80 therefore has equal applicability to the right closure system 82. The reference numerals used for the right closure system 82 will be the same as those reference numerals used on the left closure system 80 except the former reference numerals will be designated prime.

The left closure system 80 comprises a posterior strip or tape 84 and an anterior strip or tape 94. Both the posterior strip 84 and the anterior strip 94 are conventional hook and loop material with hook on one side and loop on the other side. In FIG. 3, the loop side is outwardly facing and the hook side is inwardly facing. With respect to the posterior strip 84, buckles 87, 88, and 89 are attached to the anterior edge 86 of the posterior strip 84. In addition, an auxiliary strap 92 consisting of hook and loop material (the loop side facing outwardly and the hook side facing inwardly) is attached adjacent the posterior edge 90 of the posterior strip 84. With respect to the anterior strip 94, closure straps 100, 102, and 104 are attached to the posterior edge 98 of the anterior strip 94. The closure straps 100, 102, and 104 extend through buckles 87, 88, and 89 respectively and are joined to common strap 106. The closure straps 100, 102, and 104 are constructed from an elastic material supplied under the mark VEL-STRETCH from Velcro USA Inc. The material for straps 100, 102, and 104 could also be inelastic material such as a polypropylene webbing from YKK Corporation of America, Atlanta, Ga. The choice between elastic material and inelastic material for straps 100, 102, and 104 depends on the degree of immobilization required by the patient, inelastic material for greater immobilization and elastic material for lesser immobilization.

Turning to FIG. 4, the orthosis 10 is shown assembled prior to being fit to the patient. The first step in assembling the orthosis 10 prior to fitting the patient is to attach the posterior splint 64 to the posterior web 44 by means of the attachment tabs 74 (FIG. 3) which engage the hook and loop compatible material on the external surface 48 of the posterior web 44. In addition, the anterior splint 30 is inserted into the pocket formed by the anterior middle panel 26, and the flap 28 is closed onto the anterior panel 26.

The left closure system 80 is attached to the flexible posterior member 42 by attaching the posterior strip 84 of the left closure system 80 to the left side panel 56 of the flexible posterior member 42. The auxiliary strap 92 is connected to the splint strap 66. Similarly, The right closure system 82 is attached to the flexible posterior member 42 by attaching the posterior strip 84' of the right closure system 82 to the right side panel 58 of the flexible posterior member 42. The auxiliary strap 92' is connected to the splint strap 66. The right closure system 82 is attached to the flexible anterior member 12 by attaching the anterior strip 94' to the right anterior side panel 32.

In fitting the lumbo-sacral orthosis 10 of the present invention, the side closure systems 80 and 82 are released to a fully extended condition. Next, the closure system on one side, such as left closure system 80 is left open with the anterior strip 94 of the left closure system 80 disengaged from the left anterior side panel 34 of the flexible anterior member 12. While the patient is in the standing position, the orthosis 10 is wrapped around the patient so that the posterior splint 64 is centered in the low back area of the patient. The left closure system 80 is then loosely secured to the anterior member 12 by attaching the strip 94 to the side panel 34.

Once the orthosis 10 is wrapped about the patient as described, the patient should lie in a supine position with his or her knees comfortably flexed and his or her hips and shoulders parallel. The side closure systems 80 and 82 should be adjusted making sure they are symmetrical to one another and are equal distance from the center of the flexible posterior member 42. The patient should then grasp each of the common straps 106 and 106'. The patient should then pull both straps 106 and 106' at the same time to tighten the orthosis 10 evenly and prevent any torque to the lumbar area of the spine. Once a comfortable level of compression is achieved, the common straps 106 and 106' are secured to the front panels 34 and 32 respectively.

Once the orthosis has been applied to the patient and the closure systems have been tightened to provide the appropriate level of compression, the engagement of the posterior splint 64 with the patient's spine should be observed for proper fit and alignment. In order to customize the orthosis to the individual patient, the posterior splint 64 may be removed from the posterior web 44 and molded by localized heating of the posterior splint 64. While heating posterior splint 64 to mold it to conform to the individual patient, care should be taken so that the left reinforcing ridge 70 and the right reinforcing ridge 72 are not heated to such an extent that the posterior splint 64 loses its rigidity in the direction perpendicular to the waistline 5 of the patient.

We claim:

1. A low-profile lumbo-sacral orthosis comprising:
    a. a flexible anterior member shaped to fit adjacent the waist of a patient's torso comprising:
        i. a anterior web of flexible material having an external surface and an internal surface and having a anterior middle section and two anterior side sections;
        ii. a middle panel of loop material attached to the external surface of the anterior web at the anterior middle section; and
        iii. anterior side panels of loop material attached to the external surface of the anterior web at each anterior side section;
    b. a flexible posterior member shaped to fit adjacent the waist of a patient's torso comprising:
        i. a posterior web of flexible material having an external surface and an internal surface and having a posterior middle section and two posterior side sections;
        ii. posterior side panels of loop material attached to external surface of the posterior web at each posterior side section; and
        iii. a posterior splint attached to the external surface of the posterior web at the middle section and having splint strap of loop material secured to the posterior splint and extending parallel to the waist of the patient; and
    c. a closure system on each side of the low-profile lumbo-sacral orthosis for joining the flexible anterior member to the flexible posterior member, each closure system comprising:
        i. a posterior strip of hook and loop material adapted to engage one of the posterior side panels and having a anterior edge and a posterior edge wherein a plurality of buckles are attached to the anterior edge, an auxiliary strap of hook and loop material is attached to the posterior edge, and the auxiliary strap engages the splint strap;
        ii. a anterior strip of hook and loop material adapted to engage one of the anterior side panels and having a anterior edge and a posterior edge; and
        iii. a plurality of straps attached to the posterior edge of the anterior strip, extending through the plurality of buckles on the posterior strip for attachment to the anterior side panels or anterior middle panel.

2. The low-profile lumbo-sacral orthosis of claim 1, wherein a anterior splint is interposed between the anterior middle panel and the external surface of the anterior web.

3. The low-profile lumbo-sacral orthosis of claim 2, wherein anterior reinforcing inserts are interposed between each of the anterior side panels and the external surface of the anterior web.

4. The low-profile lumbo-sacral orthosis of claim 1, wherein the posterior splint is a heat formable material with reinforcing ridges oriented in a direction perpendicular to the waistline of the patient.

5. The low-profile lumbo-sacral orthosis of claim 1, wherein posterior reinforcing inserts are interposed between each of the posterior side panels and the external surface of the posterior web.

6. The low-profile lumbo-sacral orthosis of claim 1, wherein the posterior web is dimensioned so that when the low-profile lumbo-sacral orthosis is applied to a patient, the posterior web extends from adjacent the L2 and L3 vertebrae to the sacral region of the patient's spine.

7. The low-profile lumbo-sacral orthosis of claim 1, wherein the straps of the plurality of straps attached to the posterior edge of the anterior strip are elastic.

8. The low-profile lumbo-sacral orthosis of claim 1, wherein the plurality of straps attached to the posterior edge of the anterior strip, extending through the plurality of buckles on the posterior strip terminate in a common strap of hook and loop material.

9. A low-profile lumbo-sacral orthosis comprising:
    a. a flexible anterior member shaped to fit adjacent the waist of a patient's torso comprising:
        i. a anterior web of flexible material having an external surface and an internal surface and having a anterior middle section and two anterior side sections;
        ii. a middle panel of loop material attached to external surface of the anterior web at the anterior middle section;
        iii. anterior side panels of loop material attached to external surface of the anterior web at each anterior side section;
        iv. anterior reinforcing inserts interposed between each of the anterior side panels and the external surface of the anterior web; and
        V. a anterior splint interposed between the anterior middle panel and the external surface of the anterior web;
    b. a flexible posterior member shaped to fit adjacent the waist of a patient's torso comprising:
        i. a posterior web of flexible material having an external surface and an internal surface and having a posterior middle section and two posterior side sections;
        ii. posterior side panels of loop material attached to external surface of the anterior web at each posterior of side section;
        iii. posterior reinforcing inserts interposed between each of the posterior side panels and the external surface of the posterior web; and
        iv. a posterior splint attached to the external surface of the posterior web at the posterior middle section and having a splint strap of loop material secured to the posterior splint and extending parallel to the waist of the patient; and
    c. a closure system on each side of the low-profile lumbo-sacral orthosis for joining the flexible anterior member to the flexible posterior member, each closure system comprising:
        i. a posterior strip of hook and loop material adapted to engage one of the posterior side panels and having a anterior edge and a posterior edge wherein a plurality of buckles are attached to the anterior edge, an auxiliary strap of hook and loop material is attached to the posterior edge, and the auxiliary strap engages the splint strap;

ii. a anterior strip of hook and loop material adapted to engage one of the anterior side panels and having a anterior edge and a posterior edge; and iii. a plurality of straps attached to the posterior edge of the anterior strip, extending through the plurality of buckles on the posterior strip, and terminating in a common strap of hook and loop material.

10. The low-profile lumbo-sacral orthosis of claim 9, wherein the posterior splint is a heat formable material with reinforcing ridges oriented in a direction perpendicular to the waistline of the patient.

11. The low-profile lumbo-sacral orthosis of claim 9, wherein the posterior web is dimensioned so that when the low-profile lumbo-sacral orthosis is applied to a patient, the posterior web extends from adjacent the L2 and L3 vertebrae to the sacral region of the patient's spine.

12. The low-profile lumbo-sacral orthosis of claim 9, wherein the straps of the plurality of straps attached to the posterior edge of the anterior strip are elastic.

13. The low-profile lumbo-sacral orthosis of claim 9, wherein the plurality of straps attached to the posterior edge of the anterior strip, extending through the plurality of buckles on the posterior strip terminate in a common strap of hook and loop material.

* * * * *